(12) United States Patent
Sugiyama

(10) Patent No.: US 8,597,174 B2
(45) Date of Patent: Dec. 3, 2013

(54) MEDICAL DEVICE

(75) Inventor: Yuta Sugiyama, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1138 days.

(21) Appl. No.: 12/254,302

(22) Filed: Oct. 20, 2008

(65) Prior Publication Data

US 2009/0105726 A1 Apr. 23, 2009

(30) Foreign Application Priority Data

Oct. 22, 2007 (JP) .................. 2007-274189

(51) Int. Cl.
*A61B 1/00* (2006.01)
*A61B 1/04* (2006.01)

(52) U.S. Cl.
USPC .......................... 600/104; 600/106; 600/117

(58) Field of Classification Search
USPC ................. 600/102–104, 107, 109, 117, 160
See application file for complete search history.

(56) References Cited

U.S. PATENT DOCUMENTS

| | | | |
|---|---|---|---|
| 5,339,799 A | 8/1994 | Kami et al. | |
| 5,645,585 A | 7/1997 | Kuzma | |
| 6,078,841 A | 6/2000 | Kuzma | |
| 6,905,460 B2 * | 6/2005 | Wang et al. | 600/102 |
| 2003/0212394 A1 | 11/2003 | Pearson et al. | |
| 2012/0065467 A1 * | 3/2012 | Moll et al. | 600/106 |

FOREIGN PATENT DOCUMENTS

| | | |
|---|---|---|
| DE | 42 13 426 A1 | 10/1992 |
| EP | 1 757 227 A2 | 2/2007 |
| JP | 09-168519 | 6/1997 |
| JP | 2002-065626 | 3/2002 |
| JP | 2007-061612 | 3/2007 |
| WO | WO 01/60274 A2 | 8/2001 |

* cited by examiner

*Primary Examiner* — Philip R Smith
*Assistant Examiner* — William Chou
(74) *Attorney, Agent, or Firm* — Scully, Scott, Murphy & Presser, P.C.

(57) ABSTRACT

A medical device includes: a body electrode disposed in contact with a human body; a tubular instrument having a distal electrode at a distal end portion of an insertion portion inserted into the body and a plurality of active joints for changing an orientation and a position of the distal end portion at the insertion portion; a plurality of joint position information detecting sections for respectively acquiring joint position information of the plurality of active joints; and a storage section for storing the joint position information respectively acquired by the plurality of joint position information detecting sections based on conduction between the body electrode and the distal electrode.

10 Claims, 11 Drawing Sheets

MEDICAL DEVICE

This application claims benefit of Japanese Application No. 2007-274189 filed in Japan on Oct. 22, 2007, the contents of which are incorporated by this reference.

BACKGROUND OF THE INVENTION

1. Field of the Invention

The present invention relates to a medical device including a tubular instrument having a plurality of active joints for changing a position and an orientation of a distal end portion at an insertion portion.

2. Description of the Related Art

Recently, in treatment instruments that are inserted through a treatment instrument channel provided in an endoscope, medical manipulators having a plurality of active joints at a distal end portion or the like of a treatment instrument insertion portion have been proposed for the purpose of improving operability of operators. In the medical manipulators, the distal end portion of the insertion portion is moved in an operator desired direction by pulling or loosening a drive wire by a drive actuator and rotating the active joints, for example.

An operating range of the active joints of the medical manipulator can be limited by controlling driving of the drive actuator. Therefore, when the medical manipulator is used in an operation, a given region around a diseased part is set to a reference position. By performing control to limit an operating range of a treatment unit provided in the medical manipulator, safety with respect to the diseased part can be improved.

For example, Japanese Patent Application Laid-Open Publication No. 09-168519 discloses a system and a method for mapping a catheter electrode position within a patient's body. According to the patent document, a voltage is detected between a catheter tip electrode and a reference electrode to obtain a three-dimensional location of a catheter tip within the body.

Japanese Patent Application Laid-Open Publication No. 2002-65626 discloses a novel catheter, a system and a method for detecting contact of an electrode with tissue. The system of the patent document includes a multi-electrode catheter having a location sensor and a plurality of contact electrodes, and tissue contact is detected by comparing signals between a tip electrode to a return electrode versus signal between a reference electrode to a return electrode.

Japanese Patent Application Laid-Open Publication No. 2007-61612 relates to detection of skin impedance for detecting a position of an object placed within a living body, and discloses an apparatus for detecting a position of a probe having at least one probe electrode which is adapted to be inserted into a living body. According to the patent document, electric currents are driven between a plurality of electrodes on the probe and a plurality of electrodes placed on a body surface to obtain three-dimensional position coordinates of the probe based on impedance measurements.

SUMMARY OF THE INVENTION

A medical device includes: a body electrode disposed in contact with a human body; a tubular instrument having a distal electrode at a distal end portion of an insertion portion inserted into the body and a plurality of active joints for changing an orientation and a position of the distal end portion at the insertion portion; a plurality of joint position information detecting sections for respectively acquiring joint position information of the plurality of active joints; and a storage section for storing the joint position information respectively acquired by the plurality of the joint position information detecting sections based on conduction between the body electrode and the distal electrode.

The above and other objects, features and advantages of the invention will become more clearly understood from the following description referring to the accompanying drawings.

BRIEF DESCRIPTION OF THE DRAWINGS

FIG. 1 is a view for explaining a configuration of a medical device;

FIG. 2 is a view for explaining a configuration of a distal end side portion of a treatment instrument insertion portion of a medical manipulator;

FIG. 3 is a view for explaining an example in which a distal electrode provided in a treatment instrument insertion portion of a medical manipulator is moved to a target region A;

FIG. 4 is a flowchart for explaining steps of bringing a distal electrode into contact with a target region and acquiring position information of the contact point;

FIG. 5 is a view for explaining an example in which a distal electrode of a medical manipulator is moved from a target region A to a target region B;

FIG. 6 is a view for explaining an example in which a distal electrode of a medical manipulator is brought into contact with two points on mucosa to measure a height or a depth of a diseased part;

FIG. 7 is a view for explaining another configuration and its action of a distal end side portion of a treatment instrument insertion portion of a medical manipulator;

FIG. 8 is a view for explaining a configuration example of a medical device including an electrosurgical knife unit as a treatment instrument;

FIG. 9 is a view for explaining a plurality of points acquired for setting a limited range in which a surgical knife is moved;

FIG. 10 illustrates a substantially hemispherical limited range for limiting an operating range of a surgical knife;

FIG. 11 is a view for explaining a state in which a surgical knife is moving outward from a limited range;

FIG. 13 is a view for explaining a configuration example of a medical device including an endoscope in which a distal electrode is provided on a distal end surface of an insertion portion;

FIG. 14 is a view for explaining a relationship between a distal electrode provided in an endoscope and an Oe coordinate system;

FIG. 15 is a view for explaining a state in which a distal electrode is brought into contact with mucosa.

DETAILED DESCRIPTION OF THE PREFERRED EMBODIMENTS

In the following, embodiments of the present invention will be described with reference to the drawings.

A first embodiment of the present invention will be described with reference to FIGS. 1 to 7.

Figure 1:
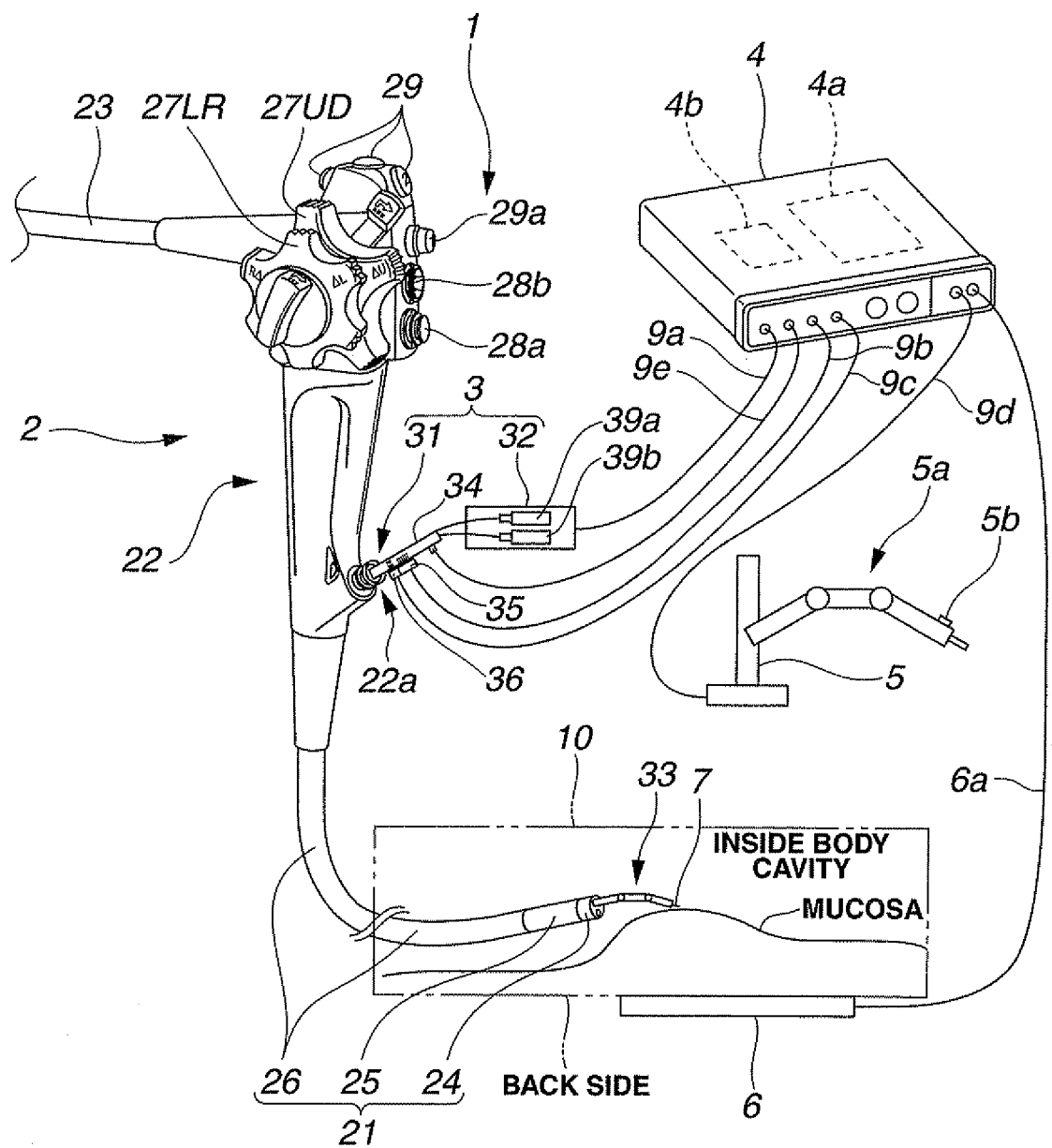
FIGS. 1 to 7 are related to a first embodiment of the present invention.

As shown in FIG. 1, a medical device I in the present embodiment includes an endoscope 2, a medical manipulator (abbreviated to treatment instrument below) 3 that is a tubular instrument, a light source and a camera control unit (not shown) which are external devices of the endoscope 2, a treatment instrument controller 4 that is a control device, a treatment instrument operating device 5, and a return electrode 6 that is a body electrode.

The endoscope 2 includes an insertion portion 21 inserted into a body cavity, an operation portion 22 provided on a proximal end side of the insertion portion 21, and a universal cord 23 extending from the operation portion 22. An unillustrated endoscope connector is provided at a proximal end portion of the universal cord 23.

The endoscope connector is connected to the light source that supplies an illuminating light. The endoscope connector is connected to the camera control unit via an image cable. An image processing circuit or the like for generating a video signal from an image signal photoelectrically converted and transmitted by an unillustrated image pickup device provided in a distal end portion of the endoscope 2 is provided in the camera control unit. The video signal generated in the image processing circuit is outputted to an unillustrated display device, so that an endoscope image is displayed on a screen of the display device.

The insertion portion 21 is constituted by a rigid distal end portion 24, a bending portion 25 that is bendable in up-and-down and right-and-left directions, for example, and a long flexible tube portion 26 having flexibility, which are sequentially provided from a distal end side.

The operation portion 22 also functions as a grasping portion. In the operation portion 22, an up and down bending knob 27UD for bending the bending portion 25 in an up and down direction, a right and left bending knob 27LR for bending the bending portion 25 in a right and left direction, an air and water supply button 28a, a suction button 28b, and a plurality of remote buttons 29 for instructing drive control or the like of an unillustrated image pickup unit provided in the distal end portion 24, or the like are provided.

A treatment instrument insertion opening 22a that constitutes a proximal end portion of an unillustrated treatment instrument channel is provided in the operation portion 22. A treatment instrument insertion portion 31 of the treatment instrument 3 described below is guided to outside of the endoscope through the treatment instrument insertion opening 22a, the treatment instrument channel (now shown) and a distal opening 24a of the distal end portion 24 shown in FIG. 2, The treatment instrument 3 includes the treatment instrument insertion portion 31 and a bending drive section 32. Drive actuators 39a and 39b are incorporated in the bending drive section 32. A stick distal electrode 7 made of metal such as stainless steel is provided at a distal end of the treatment instrument insertion portion 31.

Figure 2:
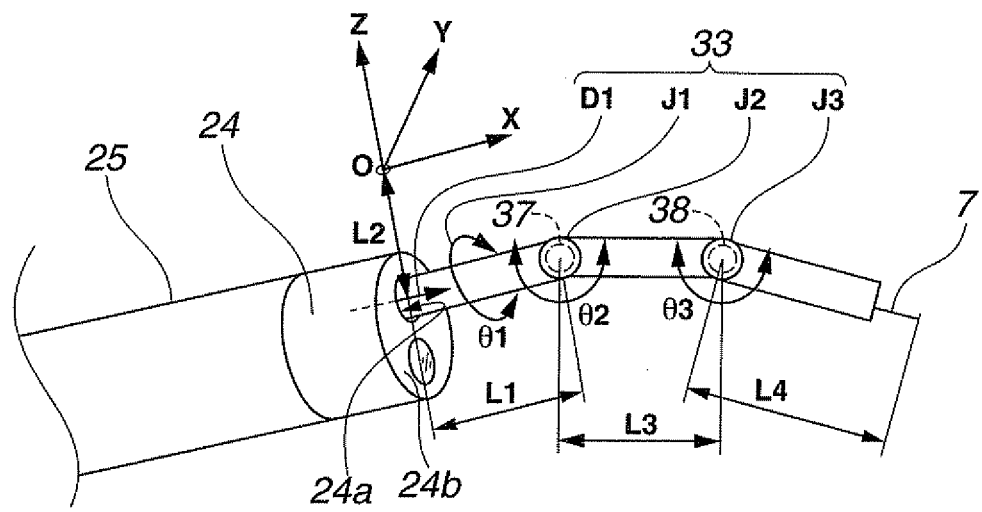

A distal bending portion 33 including a plurality of active joints shown in FIGS. 1 and 2 is provided at a distal end side portion of the treatment instrument insertion portion 31. To be more specific, the distal bending portion 33 includes a translational joint D1 that can move forward and backward with respect to an insertion direction, a first rotational joint (abbreviated to first joint below) J1 that rotates with respect to an insertion direction axis, a second rotational joint (abbreviated to second joint below) J2 that rotates with respect to an axis perpendicular to the insertion direction axis, and a third rotational joint J3 that rotates similarly to the second joint J2. That is, the treatment instrument 3 of the present embodiment is a four-degree-of-freedom active treatment instrument.

An insertion portion proximal end portion 34 is provided on a proximal end side of the treatment instrument insertion portion 31. The insertion portion proximal end portion 34 is disposed in the vicinity of the treatment instrument insertion opening 22a. A first rotary potentiometer 35 and a linear potentiometer 36, which are joint position information detecting means, are provided in the insertion portion proximal end portion 34. The first rotary potentiometer 35 measures a rotation angle $\theta 1$ of the first joint J1 that is one of the joint position information. The linear potentiometer 36 measures a translation distance L1 of the translational joint D1 that is one of the joint position information. In the present embodiment, the distance L1 is a distance from the center of the distal opening 24a to the center of the second joint J2, that is, a projecting amount of the second joint J2 from a distal end surface 24b.

On the other hand, rotary potentiometers 37 and 38 are respectively attached to the joints J2 and J3 of the distal bending portion 33 as the joint position information detecting means. The second rotary potentiometer 37 measures a rotation angle $\theta 2$ of the second joint 32 that is one of the joint position information. The third rotary potentiometer 38 measures a rotation angle $\theta 3$ of the third joint J3 that is one of the joint position information.

The joints J2 and J3 are respectively configured to rotate when an unillustrated pair of operation wires are pulled and loosened, for example. The operation wires for rotating the joints J2 and J3 are configured to be pulled and loosened by the drive actuators 39a and 39b.

In the above description, the rotary potentiometers 37 and 38 are provided to measure the rotation angles $\theta 2$ and $\theta 3$ of the joints J2 and J3. However, instead of providing the rotary potentiometers 37 and 38 in the joints J2 and J3, an encoder, a potentiometer or the like may be provided in the drive actuators 39a and 39b to measure the rotation angles $\theta 2$ and $\theta 3$. Alternatively, instead of providing the rotary potentiometers 37 and 38, a sensor for detecting a moving amount of the operation wires may be provided to measure the rotation angles $\theta 2$ and $\theta 3$.

In the present embodiment, as shown in FIG. 2, an O coordinate system is set in a predetermined position on an upper side of the drawing of the distal end surface 24b of the endoscope 2, for example. An origin O of the O coordinate system exists on a plane including the distal end surface 24b, and is set in a position apart from the center of an opening surface of the distal opening 24a by a distance L2, for example. In the present embodiment, the center of the opening surface is located on a z axis of the O coordinate system, for example.

Also, in the present embodiment, a distance between the center of the second joint J2 and the center of the third joint J3 is set to L3. Moreover, a distance from the center of the third joint J3 to a distal end of the distal electrode 7 is set to L4. The distances L3, L4 and the above distance L2 have unchangeable parameters, that is, defined values.

A position and a posture of the distal electrode 7 provided in the distal end of the treatment instrument insertion portion 31 and projecting from the distal opening 24a are represented by the O coordinate system. To be more specific, the position and posture of the distal electrode 7 in the O coordinate system are calculated by solving the forward kinematics in an arithmetic processing section, which is electrode position detecting means of the treatment instrument controller 4 described below, by providing a displacement and an angle of each joint J1, J2, J3 and D1), that is, the angles θ1, θ2 and θ3 and the distances L1, L2, L3 and L4.

On the contrary, if a target position and a target posture of the distal electrode 7 are specified by an input section 5a of the treatment instrument operating device 5 described below, the arithmetic processing section solves the inverse kinematics to calculate target values of the joints J1, J2, J3 and D1. After the calculation, a control signal generating section generates control signals for driving the joints J2 and J3 based on the results calculated in the arithmetic processing section. The drive actuators 39a and 39b are drive-controlled by the control signals to rotate the joints J2 and J3 respectively through a predetermined angle. Accordingly, the position and posture of the distal electrode 7 is changed to the target position and posture.

In the present embodiment, the treatment instrument insertion portion 31 of the treatment instrument 3 has sufficient rotation transmissibility with respect to the insertion direction axis. Also, the O coordinate system is moved and is changed to a new On coordinate system different from the O coordinate system when the insertion portion 21 of the endoscope 2 is moved forward or backward or is twisted. Therefore, position information acquired in the O coordinate system cannot be used as position coordinates of the On coordinate system.

The bending drive section 32 is connected to the treatment instrument controller 4 shown in FIG. 1 via a first connecting cord 9a, the first rotary potentiometer 35 is connected thereto via a second connecting cord 9b, the linear potentiometer 36 is connected thereto via a third connecting cord 9c, and the treatment instrument operating device 5 is connected thereto via a fourth connecting cord 9d. Reference character 9e denotes a fifth connecting cord. Signal lines respectively extending from the rotary potentiometers 37 and 38 provided in the joints 32 and J3 and an electric line extending from the distal electrode 7 are inserted into the fifth connecting cord 9e. An end portion of the fifth connecting cord 9e is connected to the treatment instrument controller 4. Accordingly, the signal lines extending from the rotary potentiometers 37 and 38 and the electric line extending from the distal electrode 7 are connected to the treatment instrument controller 4. The treatment instrument controller 4 and the above described camera control unit are connected to each other by an unillustrated signal line.

The treatment instrument controller 4 includes a control section 4a and a power section 4b, for example. The control section 4a includes a storage section that is storage means, the arithmetic processing section, and the control signal generating section that is joint control means.

The joint position information of each joint J1, J2, 33 and D1, position information of the distal electrode 7 calculated in the arithmetic processing section, or the like are stored in the storage section.

The arithmetic processing section carries out various calculations. The arithmetic processing section carries out a calculation to solve the forward kinematics for obtaining the position and posture of the distal electrode 7 in the O coordinate system based on the displacement and the angle which are the joint position information of each joint J1, J2, J3 and D1 stored in the storage section, for example. Also, the arithmetic processing section carries out a calculation to solve the inverse kinematics for obtaining the displacements and the angles of the joints J1, J2, J3 and D1 required for moving the distal electrode 7 to a point specified by the input section 5a of the treatment instrument operating device 5.

The control signal generating section generates control signals for the drive actuators 39a and 39b which rotate the joints J2 and J3 based on the calculation results obtained by solving the inverse kinematics, and outputs the control signals to the drive actuators 39a and 39b. The rotation angles θ2 and θ3 of the joints J2 and J3 are thereby changed, so that the distal electrode 7 is moved to the position specified by the input section 5a.

The treatment instrument operating device 5 includes the input section 5a. The input section 5a specifies a target distal end position (X, Y, Z) and a target posture (Roll, Pitch, Yaw) of the distal electrode 7 provided in the distal end of the treatment instrument insertion portion 31 of the treatment instrument 3. When the target distal end position (X, Y, Z) and the target posture (Roll, Pitch, Yaw) are set by the input section 5a, the control section 4a of the treatment instrument controller 4 solves the inverse kinematics using the set values by the input section 5a as described above. That is, the control section 4a calculates the target angles of the joints J2 and J3 from the setting state of the input section 5a, and the control signal generating section generates the control signals for rotating the joints J2 and J3 to output the control signals to the drive actuators 39a and 39b.

Reference character 5b denotes a contact point acquisition instruction switch (abbreviated to conducting switch below). The conducting switch 5b is provided at a distal end of the input section 5a. When a user turns ON the conducting switch 5b, the power section (see reference character 4b) of the treatment instrument controller 4 applies a predetermined voltage to the distal electrode 7 via the electric line.

The return electrode 6 is a body electrode. The return electrode 6 is attached to a back side of a patient 10, for example, so as to be in contact with a wide area thereof when the treatment instrument 3 is used or the like. A return electrode cord 6a extends from the return electrode 6. An end portion of the return electrode cord 6a is connected to the treatment instrument controller 4.

When the distal electrode 7 contacts tissue in a body in the state in which the conducting switch 5b is turned ON and the voltage is applied to the distal electrode 7, a potential difference is generated between the distal electrode 7 and mucosa. Accordingly, an electric current flows from the distal electrode 7 to the return electrode 6 via the mucosa, and the electric current returns to the treatment instrument controller 4 via the return electrode cord 6a.

In the present embodiment, when detecting the return of the electric current, the control section 4a of the treatment instrument controller 4 determines that the distal electrode 7 is contacting the mucosa. Also, at the same time as detecting the return of the electric current, the control section 4a performs control to store the joint position information of each joint J1, J2, J3 and D1 in the storage section and a process of acquiring the position information of the distal electrode described below.

Here, procedures for inserting the treatment instrument insertion portion 31 of the treatment instrument 3 into a body cavity of the patient 10 who has the return electrode 6 attached to his/her back side as shown in FIG. 1 and storing the position information of the distal electrode 7 in contact with the mucosa in the storage section are described.

First, with the insertion portion 21 of the endoscope 2 being inserted into the body cavity as shown in FIG. 1, an operator displays a target region in an endoscope image as desired and determines an observation state by performing an operation of bending the bending portion 25, twisting the insertion portion 21 or the like.

Next, the operator introduces the treatment instrument 3 through the treatment instrument channel into the body cavity. Then, the operator operates a hand side of the treatment instrument 3 to project the distal bending portion 33 of the treatment instrument insertion portion 31 from the distal end surface 24b as indicated by a solid line in FIG. 3, for example, and dispose the distal electrode 7 in the vicinity of a target region A.

Subsequently, the operator starts an operation for acquiring position information of the target region A, for example. That is, the operator turns ON the conducting switch 5b. The control section 4a thereby performs a process of applying a voltage to the distal electrode 7 of the treatment instrument 3 as shown in step S1 in FIG. 4, and a process of setting a coordinate system. In other words, the voltage is applied to the distal electrode 7, and the O coordinate system is set.

Figure 3:
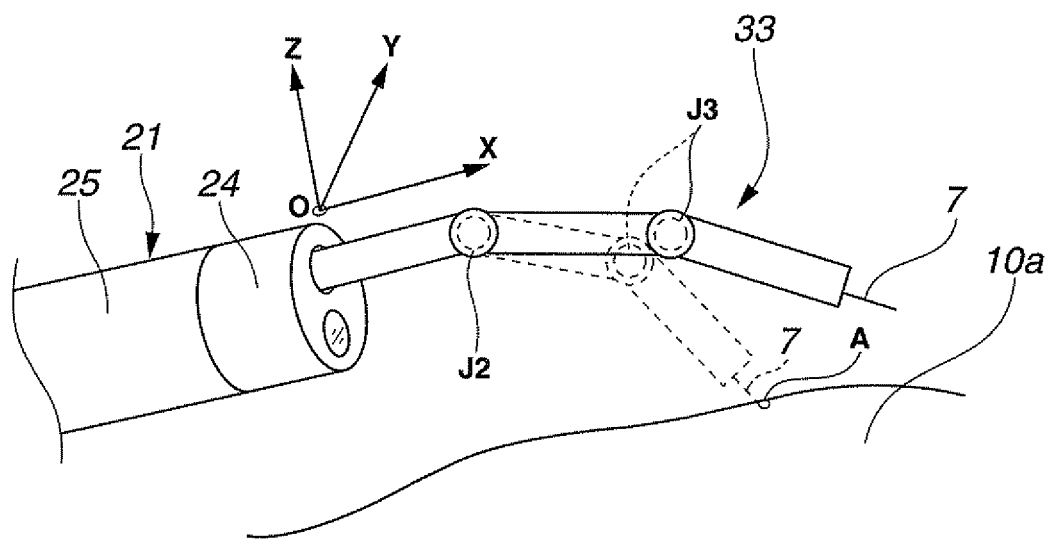
Figure 4:
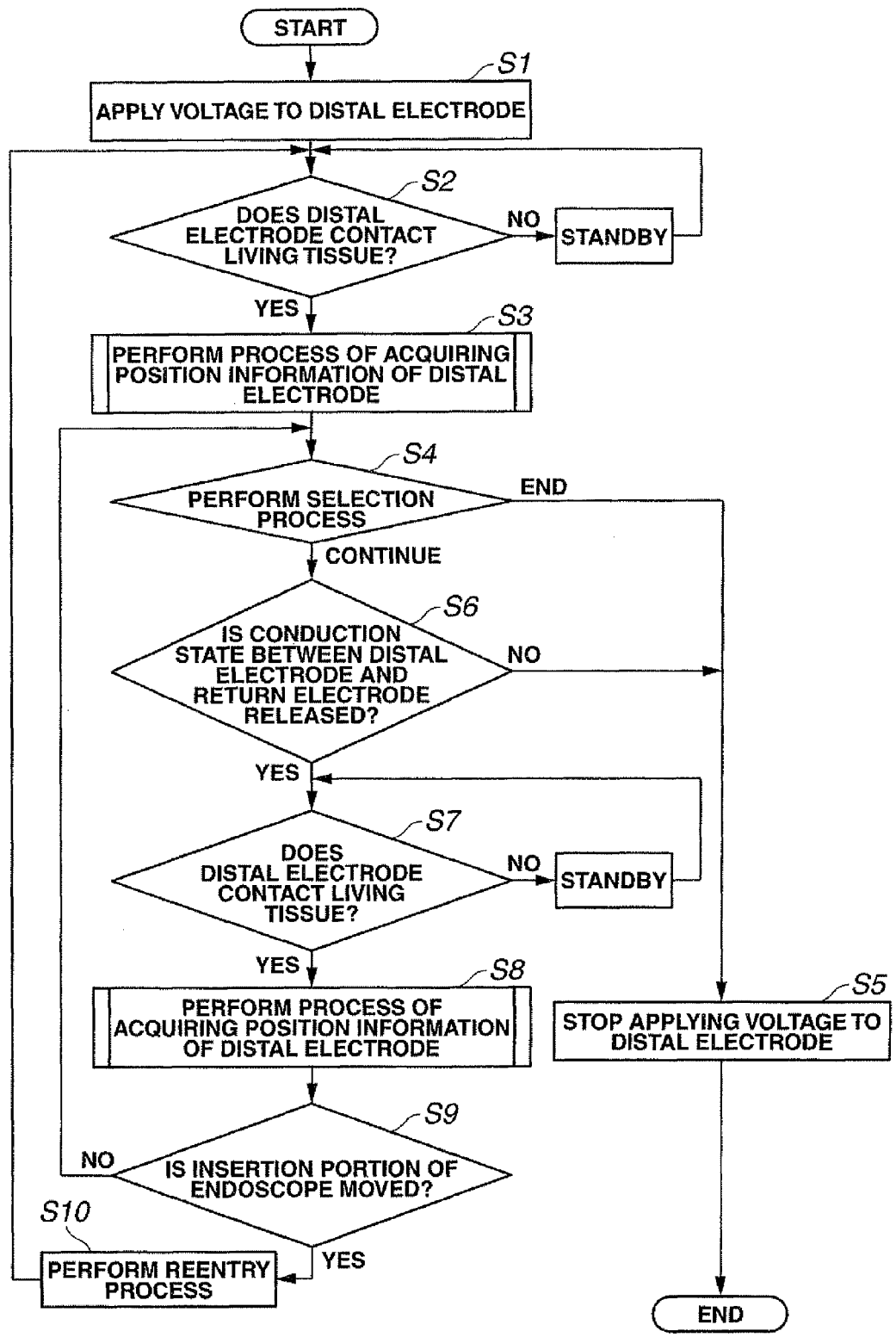

Here, the operator operates the input section 5a of the treatment instrument operating device 5 to make settings so that the distal electrode 7 contacts the target region A of mucosa 10a by moving the distal electrode 7 from a position indicated by the solid line in FIG. 3 to a position indicated by a dash line therein. According to the settings of the input section 5a, the control section 4a calculates the position and posture of the distal electrode 7, as present values, in the O coordinate system indicated by the solid line, first.

Next, the control section 4a calculates a difference between the present values and the target region A indicated by the dash line. Then, the control section 4a calculates the rotation angles of the joints J2 and J3 from the result, and generates the control signals to be supplied to the drive units for driving rotation of the joints J2 and J3. The control section 4a drives the drive actuators 39a and 39b by the generated control signals. The distal electrode 7 is thereby moved in a direction of the target region A.

Also, the control section 4a performs control shown in step S2 to step S8 after performing the process of applying a voltage to the distal electrode 7 and the process of setting the O coordinate system.

The control section 4a determines whether the distal electrode 7 contacts the target region A of the mucosa 10a as indicated by the dash line in FIG. 3 in step S2. In other words, the control section 4a determines the presence of the electric current returning to the treatment instrument controller 4 when the distal electrode 7 contacts the mucosa 10a. In the step S2, the control section 4a becomes a standby state until the electric current returns to the treatment instrument controller 4.

When confirming the contact of the distal electrode 7 with the mucosa 10a in the step S2, the control section 4a moves to step S3. In the step S3, the control section 4a starts a process of acquiring the position information of the distal electrode 7 in contact with the mucosa 10a.

The process of acquiring the position information of the distal electrode 7 in the step S3 is carried out by a storing process and a calculating process.

The storing process is a process performed at the same time as confirming the contact of the distal electrode 7 with the mucosa 10a shown in the step S2. The control section 4a stores the joint position information of each joint J1, J2, J3 and D1 measured by the potentiometers 35, 36, 37 and 38 in the storage section at the same time as confirming the contact. The control section 4a moves to the calculating process after completing the storing process.

The calculating process is a process of calculating the position information of a contact point of the distal electrode 7 in contact with the mucosa 10a by solving the forward kinematics in the arithmetic processing section based on the joint position information of the joints J1, J2, J3 and D1 stored in the storage section. The control section 4a stores the position information of the distal electrode 7 in the storage section after completing the calculating process.

The control section 4a moves to a selection process in step S4 after completing the process of acquiring the position information of the distal electrode 7 described above. The selection process is a process in which the operator selects to continue or end the acquisition of the position information.

When the end process is selected in the step 84, the control section 4a moves to step S5 to perform a process of stopping the application of voltage to the distal electrode 7. After that, the process of acquiring the position information of the target region is finished. At the time of selecting the end process, the operator turns OFF the conducting switch 5b.

On the other hand, when the continuance process is selected in the step S4, the control section 4a is in a processing state to acquire the position information of a new contact point of the distal electrode 7 with the mucosa 10a. At the timing of selecting the continuance process, the operator turns ON a button 29a that is one of the remote buttons 29 provided in the operation portion 22, for example. Then, a signal for instructing the continuance is outputted from the button 29a to the control section 4a.

Figure 5:
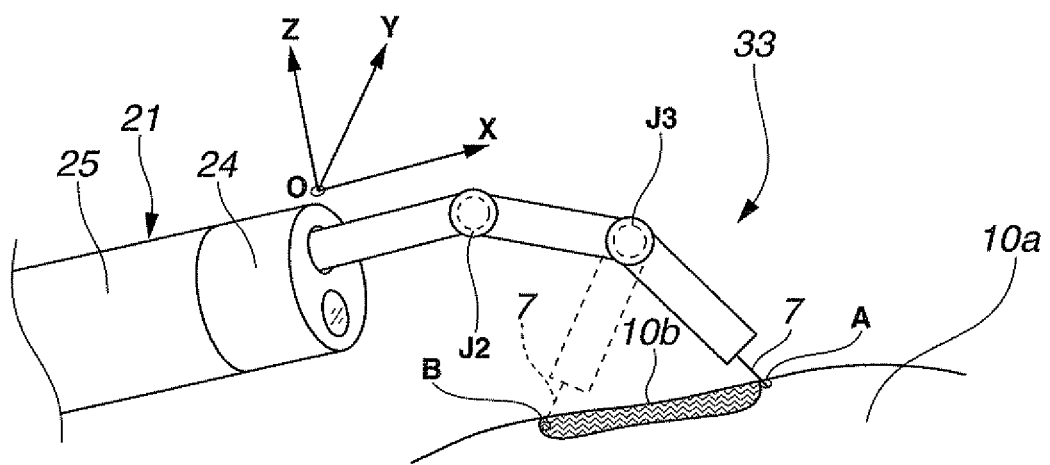

After the operator selects the continuance by turning ON the button 29a, the operator performs an operation of moving the distal electrode 7 in contact with the target region A as indicated by a solid line in FIG. 5 to a target region B indicated by a dash line therein. That is, the operator operates the input section 5a of the treatment instrument operating device 5 to release the contact of the distal electrode 7 with the mucosa 10a. Also, the operator continues to operate the input section 5a to make settings so that the distal electrode 7 contacts the new target region B of the mucosa 10a.

When detecting the signal to instruct the continuance in the step S4, the control section 4a moves to step S6, and determines whether a conduction state between the distal electrode 7 and the mucosa 10a is released. When confirming the release of the conduction state between the distal electrode 7 and the mucosa 10a in the step S6, the control section 4a moves to step S7.

In the step S7, the control section 4a determines whether the distal electrode 7 contacts the target region of the mucosa 10a in a similar manner to the above step S2. When determining that the distal electrode 7 contacts the new target region B of the mucosa 10a as indicated by the dash line in FIG. 5, the control section 4a moves to step S8 that is similar to the above step S3, and performs the process of acquiring the position information of the distal electrode 7. In the step S7, the control section 4a becomes a standby state until the electric current returns to the treatment instrument controller 4 in a similar manner to the step S2.

After acquiring the position information of a second point, for example, of the distal electrode 7 in contact with the mucosa 10a in the step S8, the control section 4a moves to step S9. In the step S9, the control section 4a determines whether a position of the insertion portion 21 of the endoscope 2 is moved based on the image signal of the signal processing circuit provided in the camera control unit, for example. That is, at the time of acquiring the position information of the second point or more, the control section 4a confirms whether the position of the insertion portion 21 of the endoscope 2 is moved based on the image signal.

When confirming that the insertion portion 21 is not moved in the step S9, the control section 4a moves to the selection process in the step S4. In the case where the continuance is selected in the step S4, the control section 4a moves to the step S6, and acquires the position information of a new contact point of the distal electrode 7 with the mucosa 10a.

On the other hand, when confirming that the insertion portion 21 is moved in the step S9, the control section 4a moves to the step S2 via a reentry process in step S10.

The reentry process in the step S10 is a process of deleting the position information of the distal electrode 7 stored in the storage section by the series of processes in the step S3 to the step S8. The reentry process is performed because a relative position of the endoscope in the body is moved to change the O coordinate system in the body, and the position information of the target regions A and B or the like stored in the storage section thereby become information indicating positions different from the positions instructed before being moved.

In the step S6, if the control section 4a cannot confirm the release of the conduction state after passage of predetermined time even though the continuation is instructed in the step S4, the control section 4a moves to the step S8 to perform the process of stopping the application of voltage to the distal electrode 7. After that, the process of acquiring the position information is finished.

As described above, the distal electrode is provided in the distal end of the treatment instrument insertion portion of the treatment instrument, and the treatment instrument insertion portion in which the distal electrode is provided is inserted into the body cavity of the patient to whom the return electrode is attached. Then, with a predetermined voltage being applied to the distal electrode, the distal electrode is brought into contact with the mucosa in the body. At this time, the conduction state is obtained at the same time as the distal electrode contacts the mucosa, and the control section can determine the conduction state. Therefore, the control section stores the joint position information of the plurality of joints in the storage section at the same time as determining the conduction, so that the position information of the distal electrode can be acquired.

Accordingly, in comparison with a case in which the operator visually determines whether the distal end of the treatment instrument insertion portion contacts a region within a body via the endoscope image and starts the process of acquiring the position information of the contact point, the process of acquiring the position information can be started with high accuracy. Also, in comparison with a case in which the operator confirms that the distal end of the treatment instrument insertion portion contacts a region within a body with a predetermined amount of force, and then, starts the process of acquiring the position information of the contact point, the process of acquiring the position information can be started with high accuracy.

Also, the acquisition of the joint position information is started at the same time as the control section determines the conduction. Therefore, an instruction to start the acquisition of the joint position information becomes unnecessary, and operability of the operator can be dramatically improved.

Furthermore, since the position information of the contact point of the distal electrode can be directly acquired as one coordinate system for controlling the joints of the treatment instrument, a coordinate transformation process or the like becomes unnecessary.

If the operator wants to obtain a length of a diseased part 10b, for example, after acquiring the position information of the target regions A and B, the operator provides the position information of the target regions A and B to the arithmetic processing section. A length L between the target regions A and B in FIG. 5 is thereby calculated in the arithmetic processing section, for example.

Figure 6:
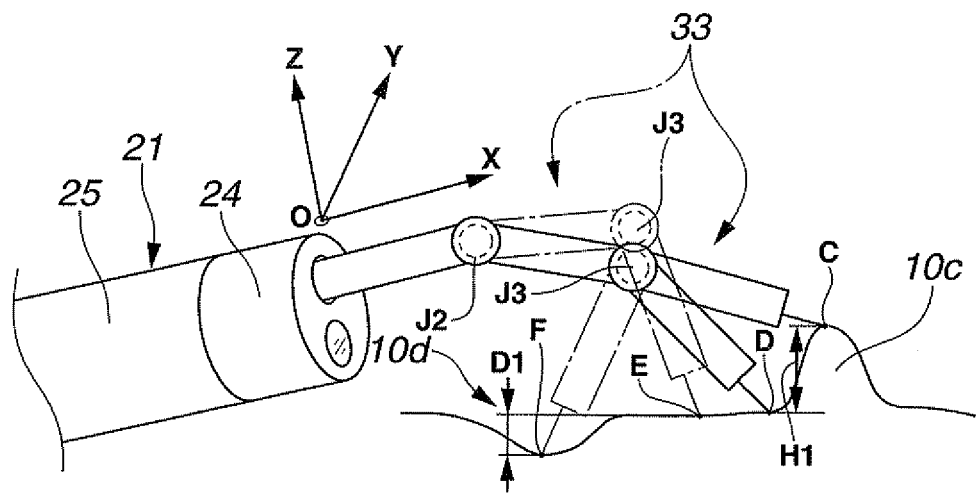

Also, the operator may measure a height dimension H of a diseased part 10c by bringing the distal electrode 7 into contact with target regions C and D of the mucosa 10a, for example, as shown in FIG. 6. Moreover, the operator may measure a depth dimension D of a diseased part 10d by bringing the distal electrode 7 into contact with E point and F point of the mucosa 10a, for example.

In the aforementioned embodiment, the distal bending portion 33 includes the translational joint D1 that can move forward and backward with respect to the insertion direction, the first joint J3 that rotates with respect to the insertion direction axis, and the second joint J2 and the third joint J3 that rotate with respect to the axis perpendicular to the insertion direction axis. However, the configuration of the distal bending portion 33 is not limited to the above configuration and a configuration of a distal bending portion 33A shown in FIG. 7 may be employed.

The distal bending portion 33A includes a fourth joint J4 perpendicular to the insertion direction axis and rotating with respect to an axis perpendicular to the axis of the joints 32 and J3 on a proximal end side from the second joint J2. A distance between the fourth joint J4 and the second joint J2 is set to a distance L5.

According to the configuration, by rotating the joint J4 to bring the distal electrode 7 into contact with G point and H point of the mucosa 10a, a so-called width dimension W can be measured in addition to the above described length dimension L1 the height dimension H and the depth dimension D.

Also, by bringing the distal electrode 7 into contact with I point, K point and so on in addition to the G point and the H point of the mucosa 10a, it becomes possible to obtain the area of a diseased part 10e enclosed by an alternate long and two short dashes line by the arithmetic processing section, for example.

A position where the fourth joint J4 is provided is not limited to the proximal end side from the second joint J2, and the fourth joint J4 may be provided between the second joint J2 and the third joint J3. In this case, a distance between the second joint J2 and the fourth joint J4, and a distance between the fourth joint J4 and the third joint J3 are respectively set to a predetermined value.

In the aforementioned embodiment, in a moment when the distal electrode 7 contacts the mucosa 10a, a stable contact state cannot be necessarily obtained at a time. That is, there sometimes occurs so-called chattering in which conduction and non-conduction are repeated in rapid cycles at the moment when the distal electrode 7 contacts the mucosa 10a. In order to prevent the chattering, electrical or software integral processing of an electric signal, low-pass filter processing, or a method of determining that the conduction is obtained when the conduction state continues for a given length of time or more and that the non-conduction is obtained when the non-conduction state continues for a given length of time or more, or the like are used.

Also, the means for acquiring the displacement of each joint D1, J1, J2, J3 and J4 is not limited to the potentiometer, and an encoder or a bend sensor may be employed, or a driving amount of the actuator may be used.

Moreover, the timing of acquiring the joint position information of each joint is not limited to the timing at the same time as detecting the conduction. The joint position information of each joint may be acquired at the same time as shifting from the conduction state to the non-conduction state.

Also, in order to prevent the O coordinate system from being changed due to the movement of the insertion portion of the endoscope, means for fixing and holding the insertion portion of the endoscope in a body may be provided. As the fixing means, a balloon may be provided at the distal end portion of the insertion portion, for example.

According to the configuration, by inflating the balloon and causing the inflated balloon to adhere to a wall surface in a body with a predetermined contact pressure, the insertion portion of the endoscope is held in the body in a stable state. Accordingly, the position information can be acquired while preventing the O coordinate system from being changed.

Also, the treatment instrument is not limited to the treatment instrument having the distal electrode at the distal end of distal bending portion, and an electrosurgical knife unit, a high-frequency cauterizing apparatus, a biopsy forceps, a grasping forceps or the like may be employed.

A second embodiment of the present invention will be described with reference to FIGS. 8 to 11. The treatment instrument of a medical device 1A in the present embodiment is an electrosurgical knife unit 3A including a surgical knife 8 at a distal end instead of the distal electrode 7. The electrosurgical knife unit 3A is equipped with a high-frequency power supply device 3B for supplying the surgical knife with high-frequency power used for high-frequency incision. The high-frequency power supply device 3B and the treatment instrument controller 4 are connected by an electric cable 9*f*. Accordingly, the control section 4*a* of the treatment instrument controller 4 can perform output control of the high-frequency power supply device 3B.

Also, in the present embodiment, the return electrode cord 6*a* is connected to the high-frequency power supply device 3B. The high-frequency power supply device 3B and the treatment instrument controller 4 are connected by a cord 9*g*. Accordingly, the control section 4*a* of the treatment instrument controller 4 can determine whether the surgical knife 8 contacts mucosa in a similar manner to the first embodiment.

Figure 7:
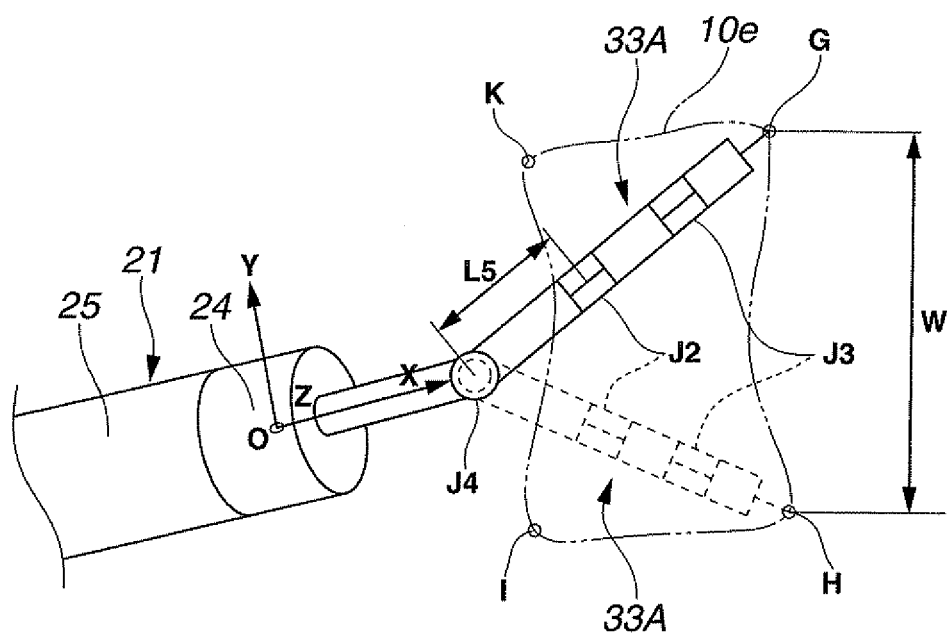
Figure 8:
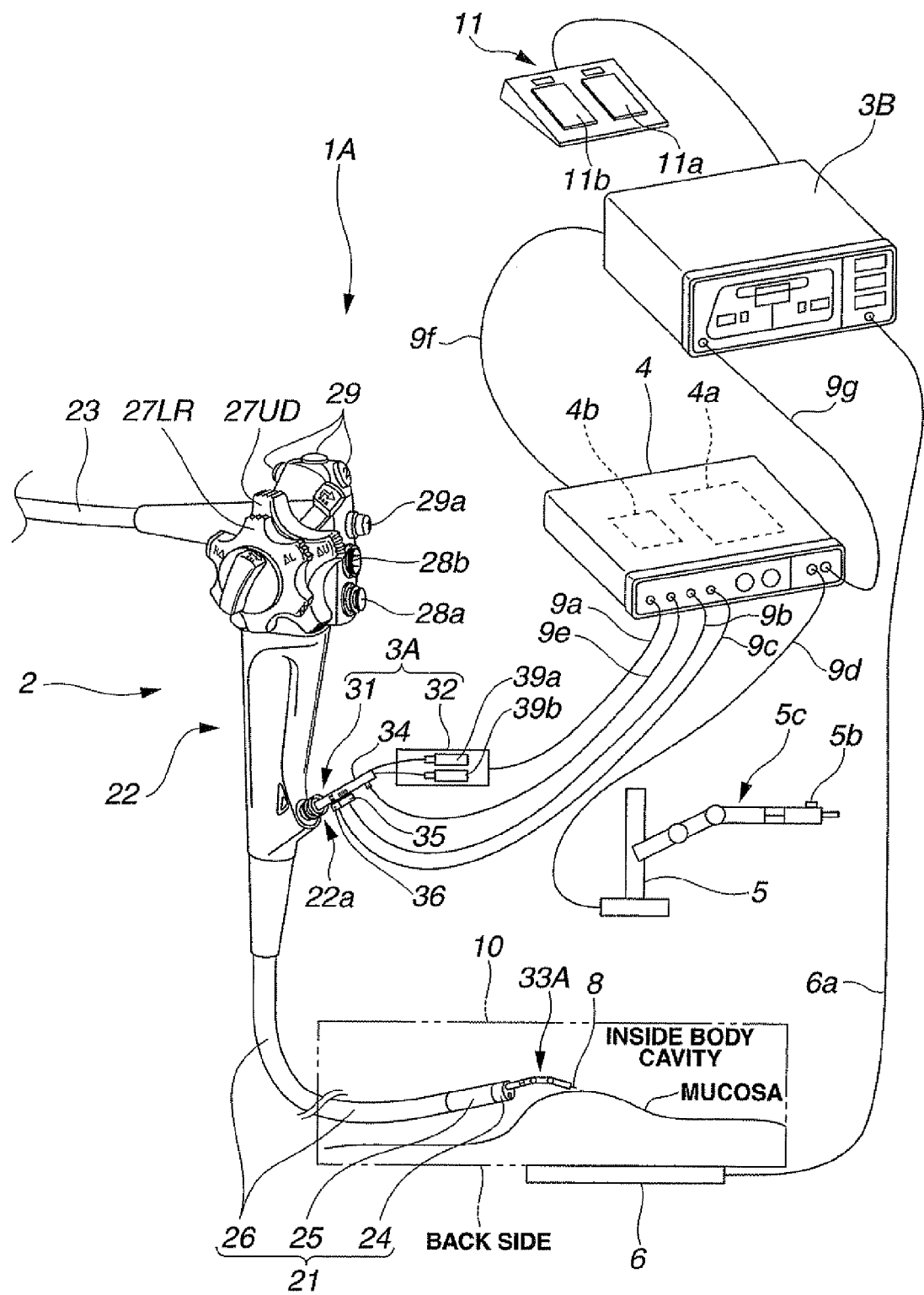
FIGS. 8 to 11 are related to a second embodiment of the present invention.

The treatment instrument insertion portion 31 of the electrosurgical knife unit 3A in the present embodiment includes the distal bending portion 33A shown in FIG. 7. Therefore, the treatment instrument operating device 5 includes an input section 5*c* corresponding to the distal bending portion 33A instead of the input section 5*a*. Reference numeral 11 denotes a foot switch. A first pedal 11*a* and a second pedal 11*b* are provided in the foot switch 11. The first pedal 11*a* instructs to start outputting the high-frequency power used for high-frequency incision. The second pedal 11*b* instructs to stop outputting the high-frequency power. The other sections in the configuration are the same as those in the first embodiment and the same members are assigned the same reference numerals to omit the description thereof.

Figure 9:
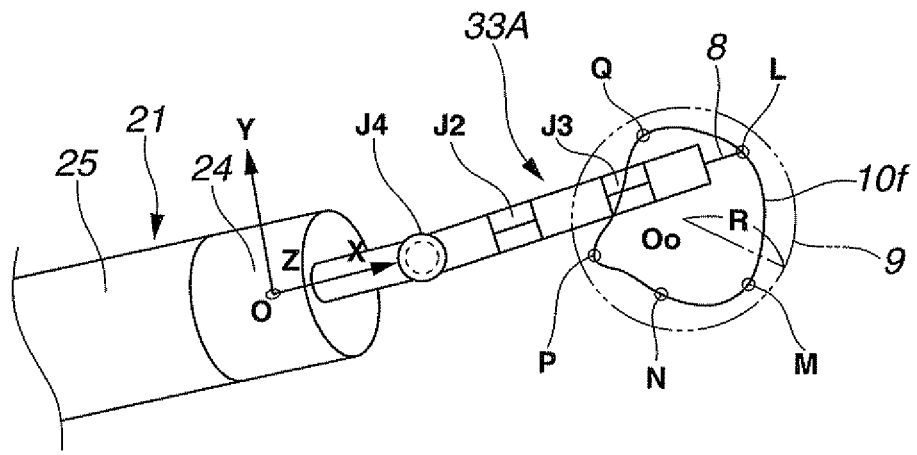
Figure 10:
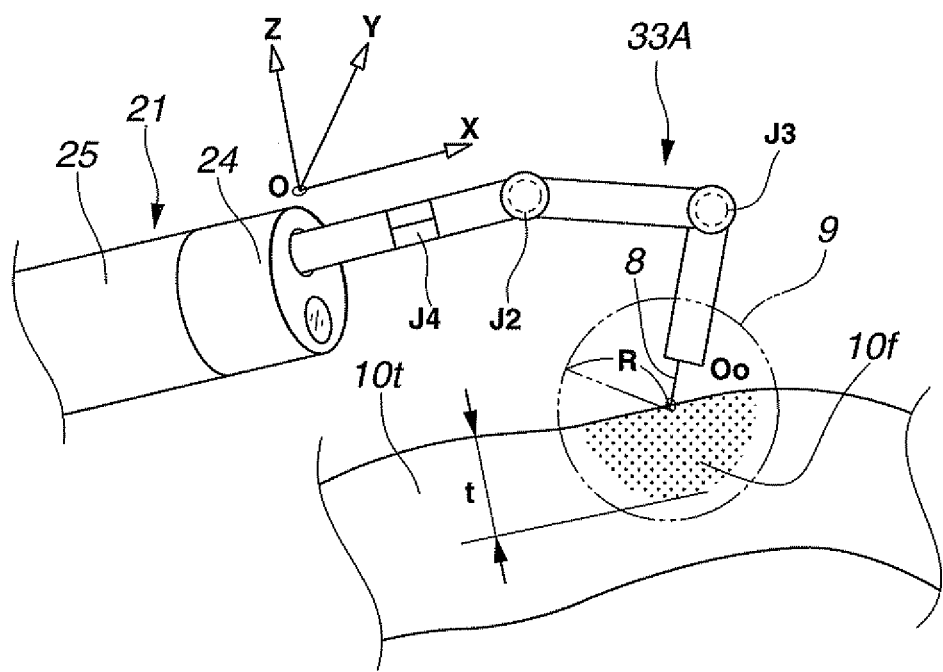

The electrosurgical knife unit 3A of the present embodiment resects a diseased part 10*f* indicated by a solid line in FIG. 9. At the time of resecting the diseased part 10*f*, an operator acquires the position information of a plurality of points such as L point, M point, N point or the like in one coordinate system with a voltage for acquiring the position information being applied to the surgical knife 8. Then, the area of the diseased part 10*f* is obtained by the arithmetic processing section based on the acquired position information of the plurality of points, for example.

Also, after acquiring the position information, the operator may acquire an operating range of the surgical knife 8 by the arithmetic processing section, for example. In this case, the operator instructs to input the plurality of position information and a resection depth or the like in consideration of a thickness t of a body wall 10*t* into the arithmetic processing section.

The arithmetic processing section of the control section 4*a* thereby calculates a limited range corresponding to the acquired position information of L point, M point, N point, P point, and Q point and the resection depth t. As a result, a spherical limited range 9 indicated by an alternate long and two short dashes line in FIGS. 9 and 10, which is constituted by a center Oo and a radius R indicated by an alternate long and two short dashes line, is obtained, for example.

When the operator confirms that the limited range 9 is set by characters or the like displayed on the screen, for example, the operator operates the first pedal 11*a* of the foot switch 11 to supply a high-frequency current from the high-frequency power supply device 3B to the surgical knife 8. Also, the operator appropriately operates the input section 5*c* of the treatment instrument operating device 5 to move the surgical knife 8 and start incision.

Figure 11:
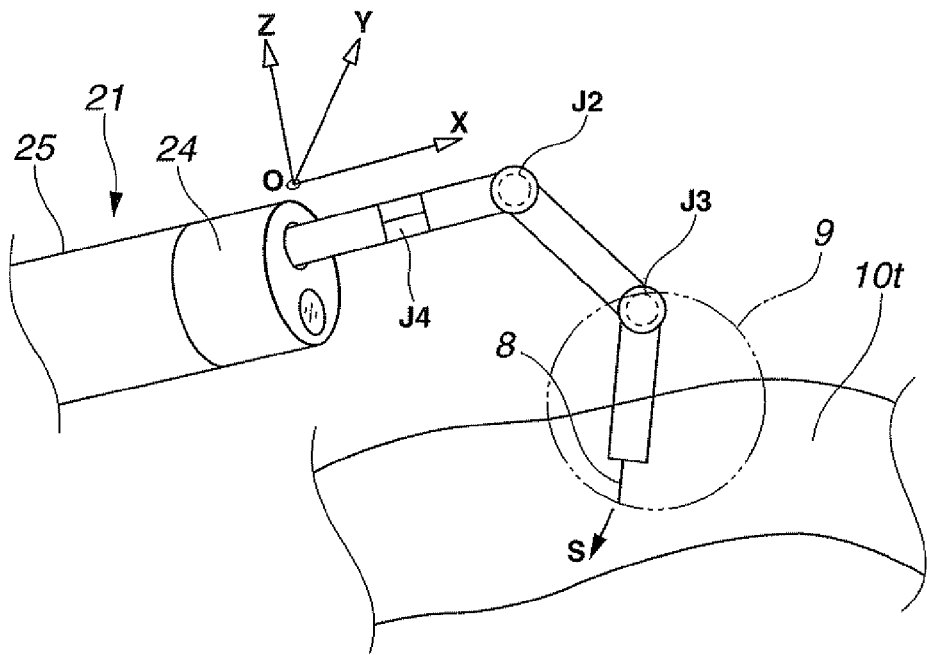

If it is instructed to move the surgical knife 8 outward from the limited range 9 as indicated by an arrow S as shown in FIG. 11 by the operation of the input section 5*c* by the operator, the control section 4*a* determines that the surgical knife 8 is approaching the limited range 9. Accordingly, the control section 4*a* performs control to slow down an operating speed of the surgical knife 8, or to intermittently or completely stop the movement of the surgical knife 8, and notifies the operator that the operator is giving an instruction to operate the surgical knife 8 to outside of the limited range. Along with giving the notification, the control section 4*a* performs control to decrease or stop the output from the high-frequency power supply device 3B, or to change its mode, so as to decrease an incision force.

By acquiring the plurality of position information in one coordinate system as described above, the limited range for limiting a range in which the surgical knife is moved in the coordinate system can be set.

Accordingly, it is possible to reliably avoid unnecessary incision even if the operator instructs to move the surgical knife outward from the limited range by mistake.

The embodiment described above requires that the position information is acquired without moving the insertion portion 21 of the endoscope 2. This is because the O coordinate system is changed to the On coordinate system and the position information acquired in the O coordinate system becomes useless information in the On coordinate system when the insertion portion 21 is moved by mistake during the acquisition of the position information.

Therefore, a method of effectively utilizing the position information acquired in the O coordinate system also in the moved On coordinate system is desired. The method of effectively utilizing the position information acquired in the O coordinate system by correlating the position information to the On coordinate system will be described with reference to FIG. 12.

Figure 12:
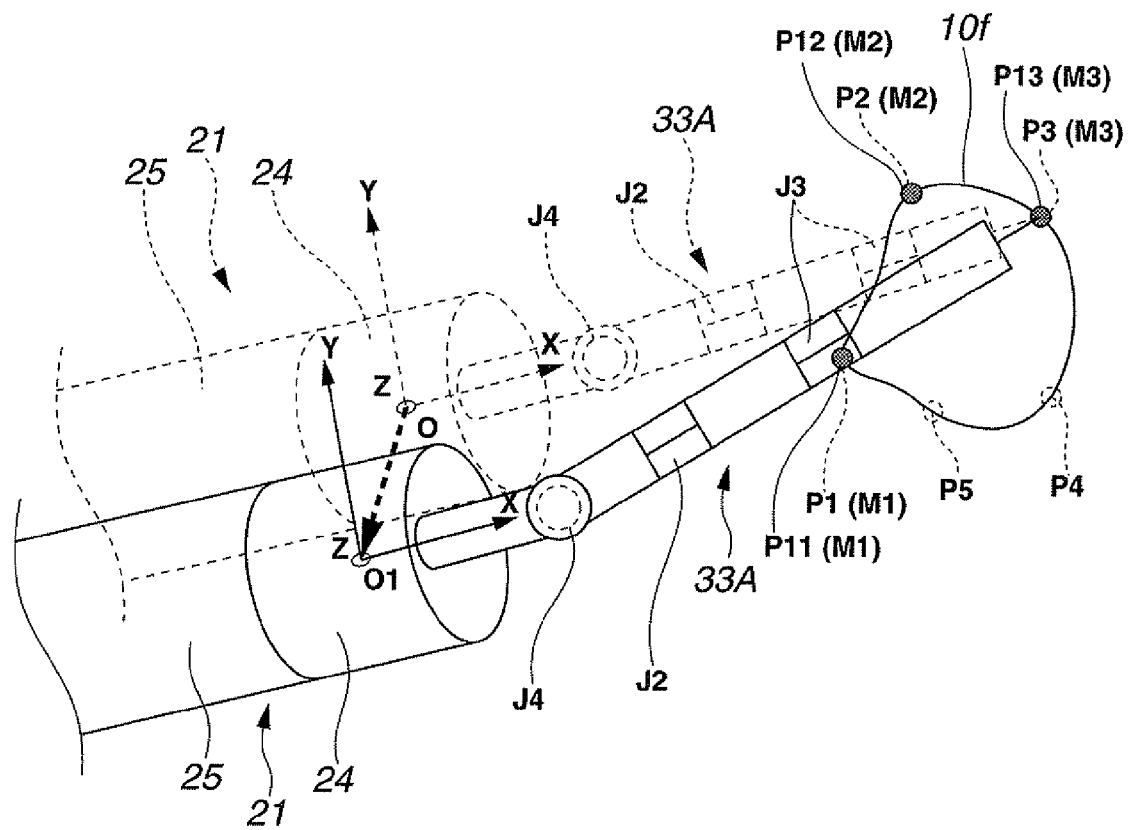
FIG. 12 illustrates marks applied to mucosa and a state in which an insertion portion is moved to a position different from a position where the marks are applied.

As shown in FIG. 12, in the present embodiment, when the position information is acquired by bringing the surgical knife 8 into contact with the diseased part 10*f*, a mark (black point in the drawing), which is visually recognized on the endoscope image, is applied to a position which the surgical knife 8 contacts at the same time as acquiring the position information. That is, in the present embodiment, the acquisition of the position information and the marking are performed when the surgical knife 8 contacts the mucosa.

To be more specific, with a voltage being applied to the surgical knife 8 by turning ON the conducting switch 5*b*, an operator operates the input section 5*c* of the treatment instrument operating device 5 to bring the surgical knife 8 into contact with a target region P1 of the mucosa. The control section 4*a* confirms that the surgical knife 8 contacts the mucosa 10*a* as shown in the above step S2. Then, the control section 4*a* acquires the position information of the surgical knife 8 in contact with the mucosa as shown in the step S3, and at the same time, performs control to supply a high-frequency current for performing the marking for a predetermined time by outputting a control signal to the high-frequency power supply device 3B. Accordingly, a first mark M1 is applied to the mucosa which the surgical knife 8 contacts.

The operator acquires the position information of the target region P1 and the first mark M1, and then, continues to acquire the position information of a target region P2 and a second mark M2, the position information of a target region P3 and a third mark M3 and so on by appropriately operating the input section 5c.

Assuming that the insertion portion 21 of the endoscope is moved from a position indicated by a dash line to a position indicated by a solid line when the operator is moving the surgical knife 8 to a target region P4 after acquiring the position information of the target region P3 and the third mark M3 while the position information and the marks in the O coordinate system are being acquired, for example, the O coordinate system of the endoscope indicated by the dash line is changed to an O1 coordinate system of the endoscope indicated by the solid line.

When the coordinate system is changed, the position information of the target regions P1, P2 and P3 acquired in the O coordinate system and stored in the storage section are not the position information of target regions P1, P2 and P3 in the changed O1 coordinate system.

Thus, when the coordinate system is changed, the operator operates a selection switch of the treatment instrument controller 4 without performing the reentry process of the above step S10. A process of correlating the position information of the target regions P1, P2 and P3 in the O coordinate system stored in the storage section to the position information in the O1 coordinate system is thereby selected. When the operator selects this process, the control section 4a sets the coordinate system to the O1 coordinate system to prompt the acquisition of two points.

The operator brings the surgical knife 8 into contact with two points of the third mark M3 and the second mark M2, for example, based on the instruction of the control section 4a. The position information of the third mark M3 and the position information of the second mark M2 in the O1 coordinate system are stored in the storage section.

When the position information of the marks M2 and M3 in the O1 coordinate system are stored in the storage section, the control section 4a instructs the arithmetic processing section to calculate an arrow indicated by a thick dash line, that is, a moving direction and a moving distance from the O coordinate system to the O1 coordinate system.

The arithmetic processing section obtains the moving direction and the moving distance from the O coordinate system to the O1 coordinate system by solving the homogeneous transformation matrix from the position information of the marks M2 and M3 in the O1 coordinate system and the position information of the target regions P2 and P3 in the O coordinate system.

As a result, the control section 4a stores in the storage section the position information of the target regions P1, P2 and P3 in the O coordinate system stored in the storage section as the position information of target regions P11, P12 and P13 in the O1 coordinate system. Accordingly, the plurality of position information acquired in the O coordinate system can be effectively utilized in the new O1 coordinate system.

As described above, when the position information is obtained by bringing the distal electrode or the surgical knife into contact with the mucosa, a plurality of position information and marks are acquired in one coordinate system by performing the acquisition of the position information and the acquisition of the marks. Accordingly, the position information acquired in one coordinate system can be utilized as the position information of another new coordinate system.

Even if a relative position and posture of the endoscope in a body are changed, the position information acquired before the position and posture of the endoscope are changed can be thereby used.

Also, according to the present embodiment a range in which the position information can be acquired is not limited to a movable range of the distal bending portion with the endoscope being fixedly held. Therefore, the position information in a wide range of the inside of a body can be acquired by changing the position and posture of the endoscope.

Furthermore, it is also possible to use the position information acquired by a grasping forceps, for example, which is another treatment instrument introduced into a body by converting the position information to the position information of the coordinate system of the electrosurgical knife unit introduced into the body.

A third embodiment of the present invention will be described with reference to FIGS. 13 to 15. A medical device 1B in the present embodiment shown in FIG. 13 includes a two-degree-of-freedom active endoscope (abbreviated to active endoscope below) 2A that is a tubular instrument, a light source and a camera control unit (not shown), a treatment instrument controller 4, a treatment instrument operating device 5 and a return electrode 6. An input section 5d corresponding to an active bending portion 25A is provided in the treatment instrument operating device 5 instead of the input sections 5a and 5c.

The active endoscope 2A includes a distal electrode 24e at a distal end surface 24b of a distal end portion 24 which constitutes an insertion portion 21. The active bending portion 25A is provided in the insertion portion 21.

Figure 13:
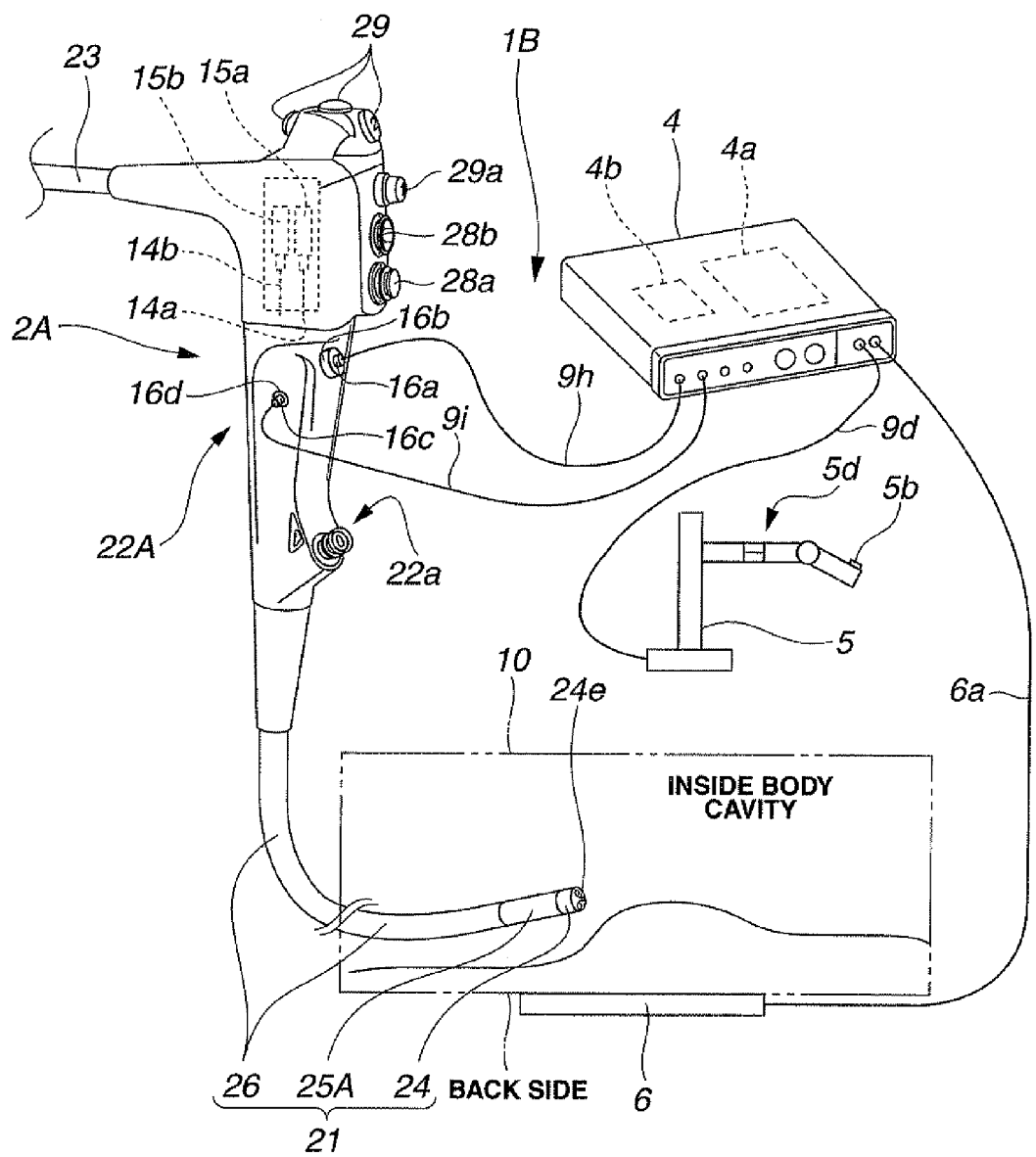
FIGS. 13 to 15 are related to a third embodiment of the present invention.
Figure 14:
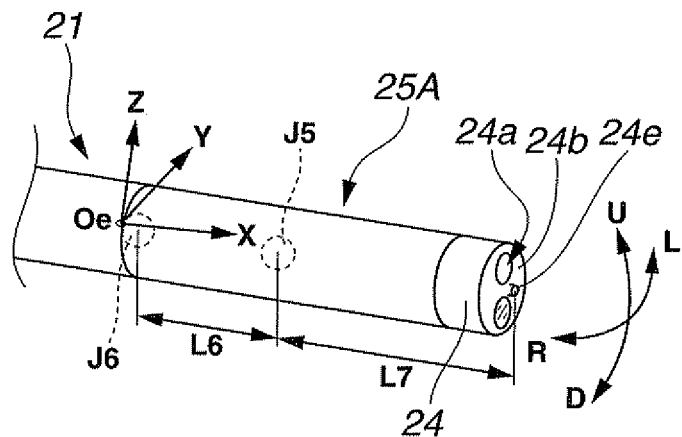

The active bending portion 25A includes a first joint J5 and a second joint J6 as shown in FIGS. 13 and 14. Also, an Oe coordinate system is set in the center on a proximal end side of the second joint J6 that is a base portion of the active bending portion 25A.

The first joint J5 is disposed on a distal end side of the active bending portion 25A. The first joint J5 rotates with respect to an axis perpendicular to an insertion direction axis to rotate the distal end surface 24b in a direction of an arrow L-R. The second joint J6 rotates with respect to an axis orthogonal to the first joint J5 to rotate the distal end surface 24b in a direction of an arrow U-D. A distance from the second joint J6 to the first joint J5 is set to a distance L6, and a distance from the first joint J5 to a distal end of the distal electrode 24e is set to a distance L7.

Also, actuators 15a and 15b for pulling and loosening operation wires 14a and 14b for moving the joints J5 and J6 are provided in an operation portion 22A of the active endoscope 2A.

Reference character 9h denotes an actuator connecting cord. By connecting a connecter portion 16a of the connecting cord 9h to a connector 16b provided in the operation portion 22A, the respective actuators 15a and 15b and the treatment instrument controller 4 are electrically connected to each other. Reference character 9i denotes an electrode cord. By connecting a connecter portion 16c of the electrode cord 9i to a connector 16d provided in the operation portion 22A, the electrode cord 9i and an electric line extending from the distal electrode 24e are electrically connected to each other.

The other sections in the configuration and the procedures for acquiring the position information are the same as those in the first embodiment, and the same members are assigned the same reference numerals to omit the description thereof.

Figure 15:
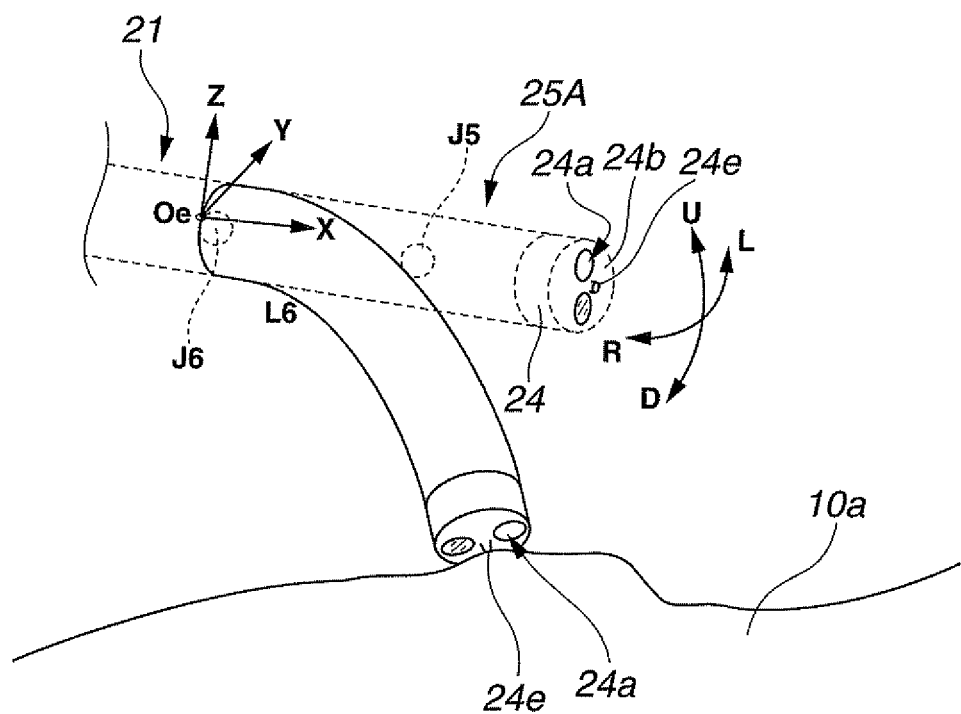

In the present embodiment, the active bending portion 25A inserted into a body cavity as indicated by a dash line in FIG. 15 is bent as indicated by a solid line therein according to the instruction of the input section 5d to bring the distal electrode 24e into contact with the mucosa 10a. At this time, the position information of a point where the distal electrode 24e contacts the mucosa 10a is stored in the storage section as the information of the Oe coordinate system.

As described above, the distal electrode is provided at the distal end surface of the insertion portion of the endoscope, and the insertion portion of the endoscope in which the distal electrode is provided is inserted into the body cavity of the patient to whom the return electrode is attached. With a predetermined voltage being applied to the distal electrode, the distal electrode is brought into contact with a target region in the body. Accordingly, the joint position information of the plurality of joints are stored in the storage section, and the position information of the distal electrode can be obtained.

Also, by appropriately setting a projection height of the distal electrode, the distal end surface and the mucosa can be brought into a desired adhesion state.

It is thereby possible to easily determine whether the distal end surface of the endoscope contacts the mucosa. Therefore, when magnification observation is performed using an active endoscope having a magnification observation mechanism, for example, the magnification observation within an observation range can be easily performed by setting a desired observation range relative to a reference point in the Oe coordinate system.

The position information of a region within a body may also be acquired by combining the active endoscope 2A and the treatment instrument 3 in the above first embodiment. By using the two active medical devices, a wide range of observation and treatment can be more safely carried out.

A configuration example of a rigid active treatment instrument will be described with reference to FIG. 16.

Figure 16:
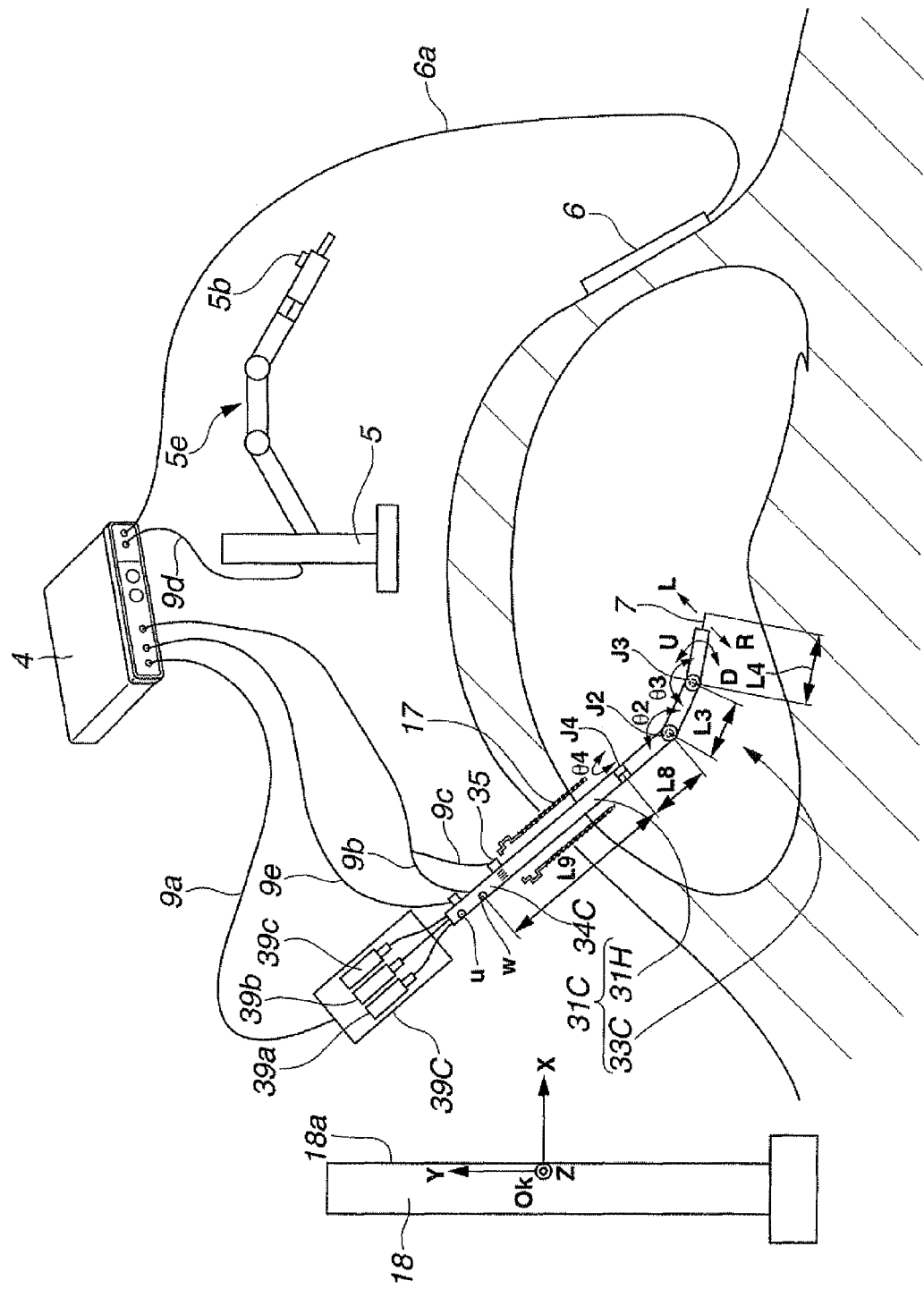
FIG. 16 is a view for explaining a rigid active treatment instrument having an active bending portion.

A rigid active treatment instrument 3C that is a tubular instrument in the present embodiment includes a treatment instrument insertion portion 31C and a bending drive section 39C as shown in FIG. 16. The treatment instrument insertion portion 31C is inserted into a body cavity through a trocar 17.

Actuators 39a, 39b and 39c for driving an active bending portion 33C described below are incorporated in the bending drive section 39C.

The treatment instrument insertion portion 31C of the rigid active treatment instrument 3C includes a rigid portion 31H and the active bending portion 33C. A distal electrode 7 is provided at a distal end of the active bending portion 33C.

The active bending portion 33C includes a first joint J4, a second joint J2, and a third joint J3 in a sequential manner from the rigid portion 31H side. The third joint J3 rotates with respect to an axis perpendicular to an insertion direction axis to rotate the distal electrode 7 in a direction of an arrow U-D. The second joint J2 rotates similar to the third joint 33 to rotate the distal electrode 7 in a direction of an arrow U-D. The first joint J4 rotates with respect to an axis orthogonal to the joints J2 and J3 to rotate the distal electrode 7 in a direction of an arrow L-R. A distance from the first joint J4 to the second joint J2 is set to a distance L8, a distance from the second joint J2 to the third joint J3 is set to a distance L3, and a distance from the third joint J3 to a distal end of the distal electrode 7 is set to a distance L4.

A proximal end portion of the rigid portion 31H of the rigid active treatment instrument 3C is configured as an insertion portion proximal end portion 34C. Light emission sections u and w are provided in the insertion portion proximal end portion 34C in addition to a rotary potentiometer 35.

An optical three-dimensional measuring device 18 includes an Ok coordinate system in substantially the center of a supporting column 18a The optical three-dimensional measuring device 18 acquires the position information of the light emission sections u and w in the Ok coordinate system. That is, by reading a change in the position information of the respective light emission sections u and w in the Ok coordinate system, a translation moving amount and a posture of the treatment instrument insertion portion 31C of the rigid active treatment instrument 3C can be acquired.

In the rigid active treatment instrument 3C, the treatment instrument insertion portion 31C is constituted by the rigid portion 31H and the active bending portion 33C. Therefore, the distances L8, L3 and L4 between each joint and a distance L9 from a distal end of the rigid portion 31H to the light emission section w, for example, which have defined values, are provided to the optical three-dimensional measuring device 18, and also, displacement amounts of rotation angles $\theta4$, $\theta2$ and $\theta3$ of the joints are provided to the optical three-dimensional measuring device 18 by connecting the treatment instrument controller 4 and the optical three-dimensional measuring device 18. Accordingly, a distal end position of the distal electrode 7 can be acquired in the Ok coordinate system without bringing the distal electrode 7 into contact with the mucosa 10a.

When the distal electrode 7 contacts the mucosa 10a, the control section of the treatment instrument controller 4 acquires the position information of a contact point in the Ok coordinate system.

The procedures for bringing the distal electrode 7 into contact with the mucosa 10a and acquiring the position information of the contact point which the distal electrode 7 contacts are the same as those in the first embodiment.

As described above, the insertion portion constitutes the rigid active treatment instrument including the rigid portion and the active bending portion. The light emission sections are provided in the insertion portion proximal end portion of the rigid active treatment instrument. Also, the optical three-dimensional measuring device capable of acquiring the change in the position of the light emission sections as the position information of one coordinate system is provided outside a body. Accordingly, the position information and posture information of the active treatment instrument inserted into the body can be obtained based on one coordinate system outside the body.

Therefore, it becomes unnecessary to fix a base portion of the active bending portion during treatment or examination, so that the position information of a wide region within the body can be acquired.

Also, by acquiring in the same coordinate system the position information in the body acquired by another rigid active treatment instrument that is inserted into the body cavity from another unillustrated trocar, the position information acquired by another rigid active treatment instrument can be effectively utilized.

A method of acquiring the position information outside a body includes a plurality of methods such as light, electric field, magnetic field, stereo camera or the like. Thus, it is easier to construct a system in comparison with the method of acquiring the position information in a body.

Also, the rigid active treatment instrument in the aforementioned embodiment may be a rigid endoscope. In this case, the distal electrode is provided at the distal end surface of the active bending portion.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device comprising:
a tubular instrument including:
an insertion portion including a distal end portion configured to be inserted into a body, and a plurality of active joints configured to change a position and a posture of the distal end portion,
a distal electrode provided at the distal end portion, and
a treatment unit provided at the distal end portion,
wherein when the treatment unit is guided into a body cavity through a treatment instrument channel of an endoscope, the plurality of active joints are configured to change a position and an orientation of the treatment unit with the endoscope being held;
a plurality of joint position information detecting sections configured to respectively acquire joint position information of the plurality of active joints;
a tubular instrument operating device including:
an input section configured to receive an input for specifying a target position and a target posture of the distal electrode, and
a contact point acquisition instruction switch configured to receive a contact point acquisition instruction for instructing to apply a predetermined voltage to the distal electrode;
a body electrode configured to be disposed on and in contact with a body surface of the body, and to receive an electric current from the distal electrode; and
a control device including:
a power section configured to apply the predetermined voltage to the distal electrode when the contact point acquisition instruction switch receives the contact point acquisition instruction, and
a control section configured to detect return of the electric current from the distal electrode to the body electrode in a state where the predetermined voltage is applied to the distal electrode, and to determine that the distal electrode is in contact with mucosa when detecting return of the electric current from the distal electrode to the body electrode.

2. The medical device according to claim 1, further comprising:
a marking section for applying a mark to mucosa with the distal electrode contacting the mucosa.

3. The medical device according to claim 2, wherein:
the marking section applies a mark, which can be visually recognized on an endoscope image, to the mucosa by supplying a high-frequency current to the distal electrode.

4. The medical device according to claim 3, wherein:
the mark is position information of the coordinate system, and when the coordinate system is changed, position information of two marks in the coordinate system before movement and position information of two marks in a coordinate system after movement corresponding to the position information of the marks are acquired to obtain movement information of the coordinate system before and after movement.

5. The medical device according to claim 1, wherein:
the tubular instrument is an endoscope having an image pickup device at the distal end portion of the insertion portion and a bending portion constituted by the active joints for changing an orientation and a position of the distal end portion.

6. The medical device according to claim 1, wherein:
the control section further includes a storage section configured to store the joint position information respectively acquired by the plurality of the joint position information detection sections, and
the control section is configured to control the plurality of joint position information detecting sections to acquire joint position information of the plurality of active joints at the time of detection of the return of the electric current from the distal electrode to the body electrode in the state where the predetermined voltage is applied to the distal electrode, and to control the storage section to store the acquired joint position information of the plurality of active joints at the time of detection of the return of the electric current from the distal electrode to the body electrode in the state where the predetermined voltage is applied to the distal electrode.

7. The medical device according to claim 6, wherein the control section further includes an electrode position detecting section for acquiring position information of the distal electrode based on the joint position information respectively acquired by the plurality of the joint position information detecting sections.

8. The medical device according to claim 7, wherein the control section further includes a joint control section for controlling the active joints based on the position information of the distal electrode acquired by the electrode position detecting section and the joint position information stored in the storage section.

9. The medical device according to claim 8, wherein the joint control section controls each of the plurality of active joints by relatively comparing the joint position information of the plurality of active joints.

10. The medical device according to claim 8, wherein the joint control section controls the active joints based on the joint position information in one coordinate system stored in the storage section and the position information of the distal electrode acquired by the electrode position detecting section to regulate the treatment unit.

* * * * *